United States Patent
Christman et al.

(10) Patent No.: US 8,352,044 B2
(45) Date of Patent: Jan. 8, 2013

(54) SYSTEMS FOR ENABLING TELEMETRY IN AN IMPLANTABLE MEDICAL DEVICE

(75) Inventors: Timothy J. Christman, Woodbury, MN (US); Jason J. Edwardson, Wyoming, MN (US); Bart A. Carey, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 228 days.

(21) Appl. No.: 12/762,086

(22) Filed: Apr. 16, 2010

(65) Prior Publication Data
US 2010/0204759 A1    Aug. 12, 2010

Related U.S. Application Data

(63) Continuation of application No. 11/423,254, filed on Jun. 9, 2006, now Pat. No. 7,720,544.

(51) Int. Cl.
*A61N 1/08* (2006.01)
(52) U.S. Cl. ............ 607/60; 607/1; 607/2; 607/32; 607/36; 343/718; 343/845; 343/872; 343/873; 128/903
(58) Field of Classification Search ............ 607/1–2, 607/32, 36, 60; 343/718, 845, 872–873; 128/903
See application file for complete search history.

(56) References Cited

U.S. PATENT DOCUMENTS

| | | | |
|---|---|---|---|
| 3,667,477 A | 6/1972 | Susset et al. | |
| 3,718,909 A | 2/1973 | Greatbatch | |
| 3,830,242 A | 8/1974 | Greatbatch | |
| 4,230,128 A | 10/1980 | Aramayo | |
| 4,262,632 A | 4/1981 | Hanton et al. | |
| 4,441,498 A | 4/1984 | Nordling | |
| 4,519,401 A | 5/1985 | Ko et al. | |
| 4,542,535 A | 9/1985 | Bates et al. | |
| 4,556,063 A | 12/1985 | Thompson et al. | |
| 4,562,841 A | 1/1986 | Brockway et al. | |
| 4,580,950 A | 4/1986 | Sumikawa et al. | |

(Continued)

FOREIGN PATENT DOCUMENTS

EP    1050265    11/2000

(Continued)

OTHER PUBLICATIONS

"U.S. Appl. No. 10/194,401, Amendment Under 37 CFR 1.312 filed Apr. 11, 2006", 5 pgs.

(Continued)

*Primary Examiner* — Carl H Layno
*Assistant Examiner* — Deborah Malamud
(74) *Attorney, Agent, or Firm* — Schwegman Lundberg & Woessner, P.A.

(57) ABSTRACT

A system for enabling telemetry in implantable medical devices is provided. One aspect of this disclosure relates to an implantable medical device having radio-frequency telemetry capabilities. The device includes a housing and electronic circuitry contained within the housing. The device also includes an antenna connected to the electronic circuitry, the antenna having a helical portion and a whip portion, the whip portion separate from a feed conductor and adapted to enhance a radiation pattern of the antenna. According to various embodiments, the antenna and circuitry are adapted to facilitate transmission and reception of modulated radio-frequency energy at a specified carrier frequency. At least a portion of the antenna is embedded in a dielectric compartment, according to various embodiments. Other aspects and embodiments are provided herein.

13 Claims, 4 Drawing Sheets

U.S. PATENT DOCUMENTS

| | | | |
|---|---|---|---|
| 4,944,299 A | 7/1990 | Silvian | |
| 5,058,581 A | 10/1991 | Silvian | |
| 5,113,869 A | 5/1992 | Nappholz et al. | |
| 5,118,825 A | 6/1992 | Wu | |
| 5,127,404 A | 7/1992 | Wyborny et al. | |
| 5,314,453 A | 5/1994 | Jeutter | |
| 5,336,245 A | 8/1994 | Adams et al. | |
| 5,337,756 A | 8/1994 | Barbier et al. | |
| 5,342,408 A | 8/1994 | deCoriolis et al. | |
| 5,385,578 A | 1/1995 | Bush et al. | |
| 5,534,019 A | 7/1996 | Paspa | |
| 5,556,421 A | 9/1996 | Prutchi et al. | |
| 5,562,713 A | 10/1996 | Silvian | |
| 5,593,430 A | 1/1997 | Renger | |
| 5,598,847 A | 2/1997 | Renger | |
| 5,650,759 A | 7/1997 | Hittman et al. | |
| 5,683,432 A | 11/1997 | Goedeke et al. | |
| 5,697,958 A | 12/1997 | Paul et al. | |
| 5,735,887 A | 4/1998 | Barreras, Sr. et al. | |
| 5,749,912 A | 5/1998 | Zhang et al. | |
| 5,766,232 A | 6/1998 | Grevious et al. | |
| 5,784,032 A | 7/1998 | Johnston et al. | |
| 5,807,397 A | 9/1998 | Barreras | |
| 5,833,603 A | 11/1998 | Kovacs et al. | |
| 5,861,019 A | 1/1999 | Sun et al. | |
| 5,862,803 A | 1/1999 | Besson et al. | |
| 5,876,331 A | 3/1999 | Wu | |
| 5,904,708 A | 5/1999 | Goedeke | |
| 5,957,854 A | 9/1999 | Besson et al. | |
| 5,958,645 A | 9/1999 | Hirose et al. | |
| 6,009,350 A | 12/1999 | Renken | |
| 6,115,634 A | 9/2000 | Donders et al. | |
| 6,115,636 A | 9/2000 | Ryan | |
| 6,116,636 A | 9/2000 | Bianchi Bazzi | |
| 6,169,925 B1 | 1/2001 | Villaseca et al. | |
| 6,205,358 B1 | 3/2001 | Haeg et al. | |
| 6,240,317 B1 | 5/2001 | Villaseca et al. | |
| 6,263,246 B1 | 7/2001 | Goedeke et al. | |
| 6,275,737 B1 | 8/2001 | Mann | |
| 6,309,350 B1 | 10/2001 | VanTassel et al. | |
| 6,329,920 B1 | 12/2001 | Morrison et al. | |
| 6,392,610 B1 | 5/2002 | Braun et al. | |
| 6,416,471 B1 | 7/2002 | Kumar et al. | |
| 6,427,088 B1 | 7/2002 | Bowman, IV et al. | |
| 6,434,429 B1 | 8/2002 | Kraus et al. | |
| 6,456,256 B1 | 9/2002 | Amundson et al. | |
| 6,470,215 B1 | 10/2002 | Kraus et al. | |
| 6,505,072 B1 | 1/2003 | Linder et al. | |
| 6,505,077 B1 | 1/2003 | Kast et al. | |
| 6,535,766 B1 | 3/2003 | Thompson et al. | |
| 6,561,975 B1 | 5/2003 | Pool et al. | |
| 6,574,508 B2 | 6/2003 | Zaouali et al. | |
| 6,574,509 B1 | 6/2003 | Kraus et al. | |
| 6,574,510 B2 | 6/2003 | Von Arx et al. | |
| 6,592,518 B2 | 7/2003 | Denker et al. | |
| 6,614,406 B2 | 9/2003 | Amundson et al. | |
| 6,622,043 B1 | 9/2003 | Kraus et al. | |
| 6,675,045 B2 | 1/2004 | Mass et al. | |
| 6,708,065 B2 | 3/2004 | Von Arx et al. | |
| 6,721,602 B2 | 4/2004 | Engmark et al. | |
| 6,766,200 B2 | 7/2004 | Cox | |
| 6,804,561 B2 | 10/2004 | Stover | |
| 6,809,701 B2 | 10/2004 | Amundson et al. | |
| 6,868,288 B2 | 3/2005 | Thompson | |
| 7,016,733 B2 | 3/2006 | Dublin et al. | |
| 7,072,718 B2 | 7/2006 | Von Arx et al. | |
| 7,103,413 B2 | 9/2006 | Swanson et al. | |
| 7,149,578 B2 | 12/2006 | Edvardsson | |
| 7,289,855 B2 | 10/2007 | Nghiem et al. | |
| 7,309,262 B2 | 12/2007 | Zart et al. | |
| 7,313,441 B2 | 12/2007 | Mass et al. | |
| 7,317,946 B2 | 1/2008 | Twetan et al. | |
| 7,319,901 B2 | 1/2008 | Dublin et al. | |
| 7,363,087 B2 | 4/2008 | Nghiem et al. | |
| 7,483,752 B2 | 1/2009 | Von Arx et al. | |
| 7,613,522 B2 | 11/2009 | Christman et al. | |
| 7,720,544 B2 | 5/2010 | Christman et al. | |
| 7,848,788 B2 * | 12/2010 | Tulley et al. | 600/423 |
| 2001/0034543 A1 | 10/2001 | Haeg | |
| 2001/0047125 A1 | 11/2001 | Quy | |
| 2002/0037756 A1 | 3/2002 | Jacobs et al. | |
| 2002/0045920 A1 | 4/2002 | Thompson | |
| 2002/0065539 A1 | 5/2002 | Von Arx et al. | |
| 2002/0095195 A1 | 7/2002 | Mass et al. | |
| 2002/0123776 A1 | 9/2002 | Von Arx et al. | |
| 2003/0023175 A1 | 1/2003 | Arzbaecher et al. | |
| 2003/0025645 A1 | 2/2003 | Amundson et al. | |
| 2003/0028095 A1 * | 2/2003 | Tulley et al. | 600/422 |
| 2003/0028902 A1 | 2/2003 | Cubley et al. | |
| 2003/0040779 A1 | 2/2003 | Engmark et al. | |
| 2003/0083719 A1 | 5/2003 | Shankar et al. | |
| 2003/0195589 A1 | 10/2003 | Von Arx et al. | |
| 2004/0027306 A1 | 2/2004 | Amundson et al. | |
| 2004/0046637 A1 | 3/2004 | Wesby Van Swaay | |
| 2004/0060011 A1 | 3/2004 | Nitta et al. | |
| 2004/0106967 A1 | 6/2004 | Von Arx et al. | |
| 2004/0123667 A1 | 7/2004 | McGrath | |
| 2004/0147969 A1 | 7/2004 | Mann et al. | |
| 2004/0147974 A1 | 7/2004 | Engmark et al. | |
| 2004/0152953 A1 | 8/2004 | Goedeke | |
| 2004/0167580 A1 | 8/2004 | Mann et al. | |
| 2004/0176811 A1 | 9/2004 | Von Arx et al. | |
| 2004/0215958 A1 | 10/2004 | Ellis et al. | |
| 2005/0027175 A1 | 2/2005 | Yang | |
| 2005/0027192 A1 | 2/2005 | Govari et al. | |
| 2005/0113886 A1 | 5/2005 | Fischell et al. | |
| 2005/0203583 A1 | 9/2005 | Twetan et al. | |
| 2005/0203584 A1 | 9/2005 | Twetan et al. | |
| 2005/0222633 A1 | 10/2005 | Edvardsson | |
| 2006/0089682 A1 | 4/2006 | Kronich et al. | |
| 2006/0224206 A1 | 10/2006 | Dublin | |
| 2006/0247711 A1 | 11/2006 | Verhoef et al. | |
| 2006/0247712 A1 | 11/2006 | Fuller et al. | |
| 2007/0142829 A1 | 6/2007 | Ahn | |
| 2007/0179554 A1 | 8/2007 | Iyer et al. | |
| 2007/0222697 A1 | 9/2007 | Caimi et al. | |
| 2007/0260294 A1 | 11/2007 | Schulman et al. | |
| 2007/0288065 A1 | 12/2007 | Christman et al. | |
| 2007/0288066 A1 | 12/2007 | Christman et al. | |
| 2008/0021522 A1 | 1/2008 | Verhoef et al. | |
| 2008/0039898 A1 | 2/2008 | Lim et al. | |
| 2009/0192574 A1 | 7/2009 | Von Arx et al. | |
| 2010/0016925 A1 | 1/2010 | Christman et al. | |

FOREIGN PATENT DOCUMENTS

| | | | |
|---|---|---|---|
| EP | 1393672 A1 | 3/2004 | |
| EP | 1537895 A1 | 6/2005 | |
| EP | 1362614 B1 | 3/2008 | |
| WO | WO-9848895 A1 | 11/1998 | |
| WO | WO-0062664 A1 | 10/2000 | |
| WO | WO-0180731 A1 | 11/2001 | |
| WO | WO-0191428 A2 | 11/2001 | |
| WO | WO-0231909 A1 | 4/2002 | |
| WO | WO-02089667 A1 | 11/2002 | |
| WO | WO-03053515 A1 | 7/2003 | |
| WO | WO-2004066834 A1 | 8/2004 | |
| WO | WO-2005123186 | 12/2005 | |
| WO | WO-2006060750 A1 | 6/2006 | |
| WO | WO-2006131302 A1 | 12/2006 | |

OTHER PUBLICATIONS

"U.S. Appl. No. 10/194,401, Final Office Action mailed Dec. 28, 2005", 8 pgs.

"U.S. Appl. No. 10/194,401, Non Final Office Action mailed Jun. 29, 2005", 4 pgs.

"U.S. Appl. No. 10/194,401, Response filed Feb. 28, 2006 to Final Office Action mailed Dec. 28, 2005", 7 pgs.

"U.S. Appl. No. 10/194,401, Response filed Sep. 29, 2005 to Non Final Office Action mailed Jun. 29, 2005", 7 pgs.

"U.S. Appl. No. 10/252,494, Non-Final Office Action mailed Jan. 30, 2003", 4 pgs.

"U.S. Appl. No. 10/252,494, Notice of Allowance mailed Mar. 25, 2003", 5 pgs.

"U.S. Appl. No. 10/252,494, Response filed Mar. 5, 2003 to Non Final Office Action mailed Jan. 30, 2003", 6 pgs.

"U.S. Appl. No. 10/634,233, Notice of Allowance mailed Jun. 16, 2004", 6 pgs.

"U.S. Appl. No. 10/800,596, Amendment and Response filed Jun. 7, 2007 to Final Office Action mailed Mar. 7, 2007", 8 pgs.

"U.S. Appl. No. 10/800,596, Final Office Action mailed Dec. 4, 2007", 4 pgs.

"U.S. Appl. No. 10/800,596, Final Office Action mailed Mar. 7, 2007", 7 pgs.

"U.S. Appl. No. 10/800,596, Non-Final Office Action mailed Mar. 3, 2008", 9 pgs.

"U.S. Appl. No. 10/800,596, Non-Final Office Action mailed Jun. 28, 2007", 6 pgs.

"U.S. Appl. No. 10/800,596, Notice of Allowance mailed Sep. 17, 2008", 4 pgs.

"U.S. Appl. No. 10/800,596, Response filed Feb. 4, 2008 to Final Office Action mailed Dec. 4, 2007", 6 pgs.

"U.S. Appl. No. 10/800,596, Response filed Jun. 3, 2008 to Non-Final Office Action mailed Mar. 3, 2008", 8 pgs.

"U.S. Appl. No. 10/800,596, Response filed Sep. 28, 2007 to Non-Final Office Action mailed Jun. 28, 2007", 8 pgs.

"U.S. Appl. No. 11/423,254, Non-Final Office Action mailed Jul. 28, 2009", 10 pgs.

"U.S. Appl. No. 11/423,254, Notice of Allowance mailed Dec. 31, 2009", 8 pgs.

"U.S. Appl. No. 11/423,254, Response filed Apr. 30, 2009 to Restriction Requirement filed Mar. 31, 2009", 11 pgs.

"U.S. Appl. No. 11/423,254, Response filed Oct. 28, 2009 to Non Final Office Action mailed Jul. 28, 2009", 14 pgs.

"U.S. Appl. No. 11/423,254, Restriction Requirement mailed Mar. 31, 2009", 9 pgs.

"U.S. Appl. No. 11/423,262 Response filed Mar. 24, 2009 to Non Final Office Action mailed Dec. 24, 2008", 9 pgs.

"U.S. Appl. No. 11/423,262, Non-Final Office Action mailed Dec. 24, 2008", 9 pgs.

"U.S. Appl. No. 11/423,262, Notice of Allowance mailed Jun. 23, 2009", 7 pgs.

Karacolak, T., et al., "Design of a Dual-Band Implantable Antenna and Development of Skin Mimicking Gels for Continuous Glucose Monitoring", *IEEE Transactions on Microwave Theory and Techniques*, 56(4), (Apr. 2008), 1001-1008.

"U.S. Appl. No. 12/565,482, Non Final Office Action mailed Dec. 22, 2011", 15 pgs.

"U.S. Appl. No. 12/565,482, Response filed Mar. 19, 2012 to Non Final Office Action mailed Dec. 22, 2011", 20 pgs.

"U.S. Appl. No. 12/565,482, Final Office Action mailed Jun. 21, 2012", 8 pgs.

"U.S. Appl. No. 09/798,249, Non-Final Office Action mailed Mar. 28, 2003", 7 pgs.

"U.S. Appl. No. 09/798,249, Notice of Allowance mailed Oct. 21, 2003", 5 pgs.

"U.S. Appl. No. 09/798,249, Response filed Jul. 28, 2003 to Non Final Office Action mailed Mar. 28, 2003", 8 pgs.

"U.S. Appl. No. 09/921,653, Notice of Allowance mailed May 7, 2002", 6 pgs.

"U.S. Appl. No. 10/194,401, Notice of Allowance mailed Mar. 6, 2006", 4 pgs.

* cited by examiner

US 8,352,044 B2

SYSTEMS FOR ENABLING TELEMETRY IN AN IMPLANTABLE MEDICAL DEVICE

CROSS REFERENCE TO RELATED APPLICATION

This application is a continuation of U.S. application Ser. No. 11/423,254, now issued as U.S. Pat. No. 7,720,544, filed Jun. 9, 2006, which is hereby incorporated by reference in its entirety.

TECHNICAL FIELD

This disclosure relates to implantable medical devices, particularly systems for enabling telemetry in implantable medical devices.

BACKGROUND

Certain implantable medical devices (IMDs) have the capability to communicate data with an external communication, monitoring or control device via a telemetry link. Examples include cardiac rhythm management devices such as pacemakers and implantable cardioverters/defibrillators, and neurostimulators. Data typically transmitted between an external device and an IMD includes operating parameters, stimulus and sensing modes and physiological data.

In previous telemetry systems, the IMD and the external device communicated by generating and sensing a modulated magnetic field between the devices, with the antennas of the respective devices inductively coupled together and adapted for near-field communication. The external device included a wand having an antenna, and the wand had to be in close proximity to the IMD, typically within a few inches, in order for communications to take place.

Thus, there is a need for systems for enabling longer distance, higher data rate telemetry in implantable medical devices.

SUMMARY

Disclosed herein, among other things, is an implantable medical device having radio-frequency telemetry capabilities. The device includes a housing and electronic circuitry contained within the housing. The device also includes an antenna connected to the electronic circuitry, the antenna having a helical portion and a whip portion, the whip portion separate from a feed conductor and adapted to enhance a radiation pattern of the antenna. According to various embodiments, the antenna and circuitry are adapted to facilitate transmission and reception of modulated radio-frequency energy at a specified carrier frequency. The antenna is adapted for far-field communication, according to various embodiments.

A device embodiment includes a housing for containing electronic circuitry. The device also includes a header adjacent a housing surface and a dielectric compartment adjacent a housing surface and adjacent the header. An antenna is connected to the electronic circuitry, the antenna having a helical portion embedded in the header and a whip portion embedded in the dielectric compartment. According to various embodiments, the antenna and circuitry are adapted to facilitate transmission and reception of modulated radio-frequency energy at a specified carrier frequency. The antenna is adapted for far-field communication, according to various embodiments.

One aspect of this disclosure relates to a method for making an IMD having radio-frequency telemetry capabilities. According to various embodiments, the method includes forming an antenna assembly, including forming an antenna having a helical portion and a whip portion, the whip portion separate from a feed conductor. The method embodiment also includes installing the antenna assembly in an implantable medical device. The method embodiment further includes connecting the antenna assembly to electronic circuitry within the implantable medical device. The antenna can be surrounded with a dielectric material before or after it is installed into the device, according to various embodiments.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.

The present disclosure provides a system for enabling radio-frequency telemetry in implantable medical devices (IMD). Examples of IMDs include, but are not limited to: cardiac rhythm management devices such as pacemakers and implantable cardioverters/defibrillators; passive implantable monitoring devices; peripheral devices such as weight scales or blood pressure monitors; and neurostimulators. An antenna for use with an IMD is provided. The antenna includes at least a helical portion and a whip portion, which allows the radiation pattern of the antenna to be altered and made more uniform. A helical antenna would have limited off-axis radiation, and the whip portion allows for a more omnidirectional radiation pattern. Specifically, a helical antenna may be configured for greater off-axis radiation by transmitting at a wavelength much larger than the dimensions of the helix, but this decreases the efficiency of the antenna. Also, the whip portion can provide a reduction in nulls in the antenna response due to the shadow effect of the housing.

In addition, the use of the two segments allows for impedance matching and provides a greater effective length for the resulting antenna. The parasitic inductance of the helical segment allows the use of a whip portion that is physically shorter than the equivalent monopole alone, at a given carrier frequency. Thus, the helical segment makes the antenna appear electrically longer than an equivalent monopole, which allows for antennas that can be optimized over an octave of tuning range without sacrificing valuable space on the IMD. Thus, the helical portion can be physically and electrically shorter than a quarter of a wavelength of an electromagnetic wave propagating through a tissue medium having a relative dielectric constant greater than a free space relative dielectric constant.

The present disclosure provides: greater range for reliable, high-speed communication with an IMD; more uniform radiation performance, independent of device orientation or surroundings; improved tuning for specific media; and consistent operation across a broad range of frequencies and dielectric terminations.

Figure 2:
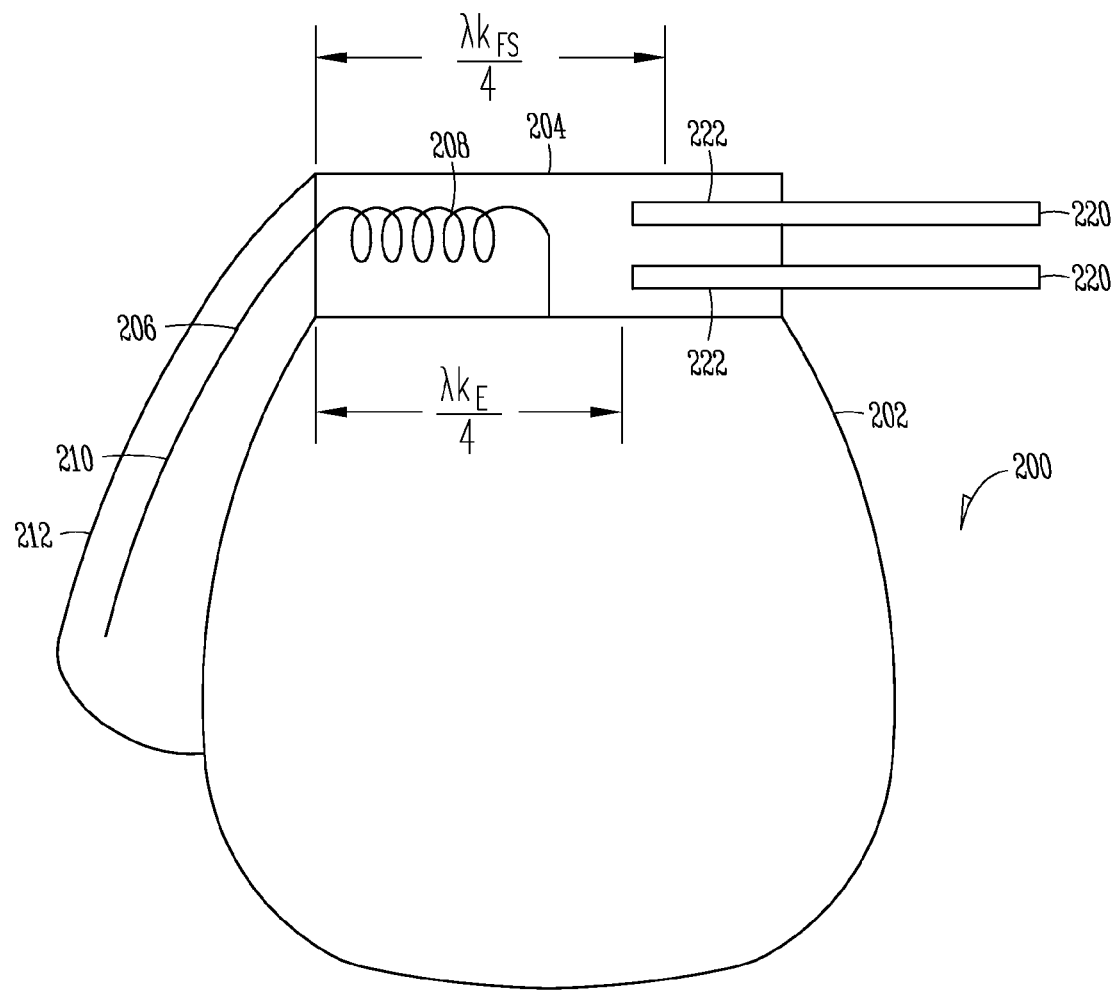
FIG. 2 illustrates an implantable medical device having a dielectric compartment, according to one embodiment.

The parasitic inductance of the helical portion 208 allows the use of the whip portion 210 that is physically shorter than the equivalent monopole alone, at a given carrier frequency. Thus, the helical portion 208 makes the antenna 206 appear electrically longer than an equivalent monopole, which allows for antennas that can be optimized over an octave of tuning range without sacrificing valuable space on the IMD. For example, as depicted conceptually in FIG. 2, the helical portion 208 can be physically and electrically shorter than a quarter of a wavelength ($\lambda/4$) of an electromagnetic wave propagating through a tissue medium having a relative effective dielectric constant ($k_E$) greater than a free space ($k_{FS}$) relative dielectric constant. In FIG. 2, $\lambda k_{FS}/4$ can represent a quarter wavelength in free space, and $\lambda k_E/4$ can represent a quarter wavelength corresponding to an effective dielectric constant ($k_E$) established when the antenna is in a tissue medium.

Implantable Medical Devices

Figure 1A:
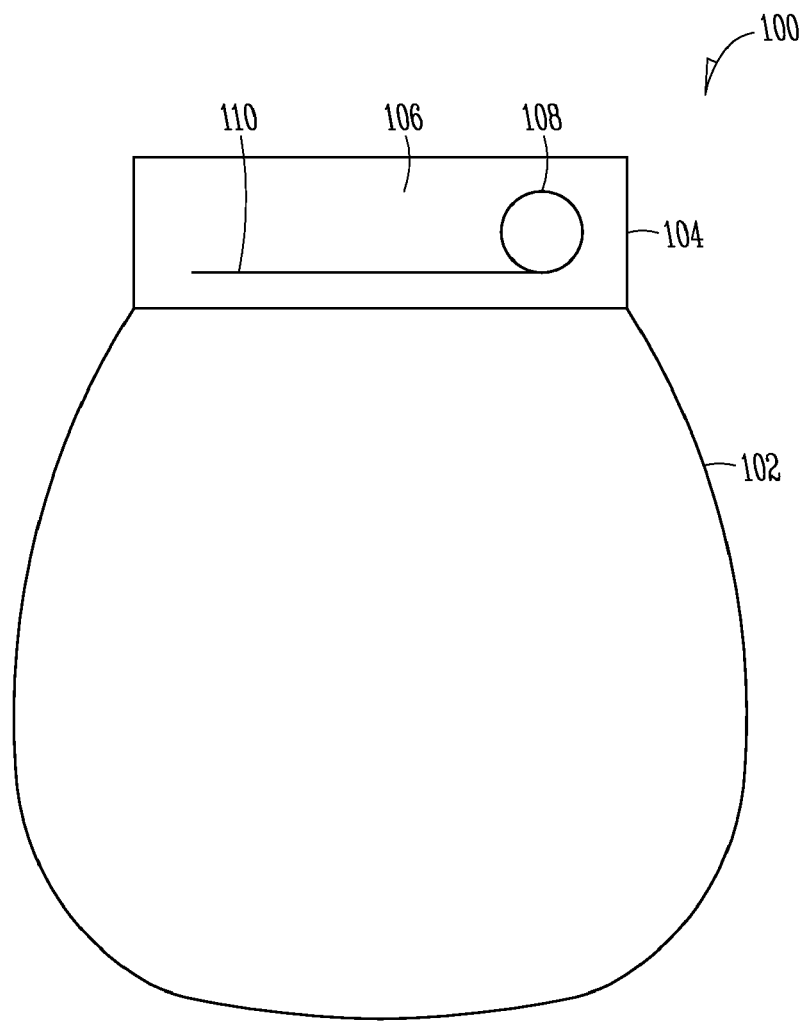
FIG. 1A illustrates a side view of an implantable medical device having radio-frequency telemetry capabilities, according to one embodiment.

FIG. 1A illustrates a side view of an implantable medical device having radio-frequency telemetry capabilities, according to one embodiment. The device 100 includes a housing 102 for containing electronic circuitry. The device also includes an antenna 106 connected to the electronic circuitry, the antenna 106 having a helical portion 108 and a whip portion 110, the whip portion separate from a feed conductor and adapted to enhance a radiation pattern of the antenna. According to various embodiments, the antenna and circuitry are adapted to facilitate transmission and reception of modulated radio-frequency energy at a specified carrier frequency. The antenna is adapted for far-field communication, according to various embodiments. Specifically, the antenna is adapted such that the return loss is minimized at the carrier frequency, and the overall radiation efficiency is optimized for tissue. For example, when surrounded by a muscle tissue simulant fluid at a depth of 3 cm, the radiation efficiency is greater than 1%. This optimization occurs when the antenna provides a conjugate match to the output impedance of a radio frequency input/output block and waveguiding structure that feeds the antenna. The number of turns on the helical portion, pitch between turns, radius of the helix, length of the whip portion, width or diameter of the whip portion and separation of helical and whip portions from the housing or other metallic structures will also influence the impedance.

In various embodiments, the specified carrier frequency includes frequencies within the range from 300 MHz to 1 GHz. The antenna can be scaled for other frequency ranges, in various embodiments. For example, frequencies in S-band (ranging from 2.0-4.0 GHz) or frequencies in X-band (ranging from 8.0-12.0 GHz) can be used as the carrier frequency, according to various embodiments. The helical portion generally has the shape of a helix, but may include antenna geometries such as spirals or coils in various embodiments. The helical portion is between the whip portion and the feed conductor, according to various embodiments.

According to various embodiments, the antenna is embedded in a dielectric compartment. The compartment can be included in a header 104 adjacent a housing surface, according to an embodiment. The header can be adapted to connect to one or more leads having one or more electrodes adapted to deliver electrical therapy. According to one embodiment, the compartment includes a pocket within the housing. The compartment can be partially or completely comprised of a dielectric material. The dielectric material in the compartment can be the same or different than the dielectric material in the device header. According to an embodiment, the dielectric material in the compartment has a higher relative dielectric constant to facilitate more efficient coupling of radiation into a surrounding implant medium of high dielectric constant material, such as when the device is implanted in or adjacent to muscle tissue. According to various embodiments, the dielectric material can include a sleeve of alumina, a sleeve of a ceramic, or a high-dielectric constant liquid or tissue in a sleeve surrounding the antenna.

Lead bores protrude from the device header, according to various embodiments. In one embodiment, the antenna is positioned within the header opposite the lead bore, to take advantage of dead space within the header and to decrease the impact of changes in lead configuration. The device also includes a feed conductor adapted to provide an electrical connection between the electronic circuitry and the antenna, according to various embodiments. In addition, the feed conductor can be adapted to connect to the antenna at a point along the antenna selected for optimal transmitting and receiving of radio-frequency energy at a specified frequency, or over a specified range of frequencies.

The device also includes a return structure attached to the antenna. The return structure may be adapted to provide a conductive return path connected to the electronic circuitry or the device housing, according to various embodiments. The return structure may be adapted to provide a capacitive return path in various embodiments. In one embodiment, the antenna provides a capacitive return path through reactive coupling to a nearby conductive grounding structure connected to the electronic circuitry or the housing. The return structure can include a conductor suspended in a dielectric a predetermined distance from the housing to prevent high-voltage arc-over during therapy delivery, and positioned to maximize the reactive coupling of the radio frequency energy from the return structure to the housing forming a low impedance path over a selected range of frequencies. The feed and return structures, which provide electrical connection between the antenna and the electronic circuitry in the housing, need not be helical, and may be comprised of linear segments, plates, or other suitable geometry. The device may also include a frequency selective isolation transformer adapted to isolate the feed conductor and the return structure from therapy voltages, according to various embodiments.

According to one embodiment, the device also includes a switch adapted to isolate the feed conductor and the return structure from therapy voltages.

Figure 1B:
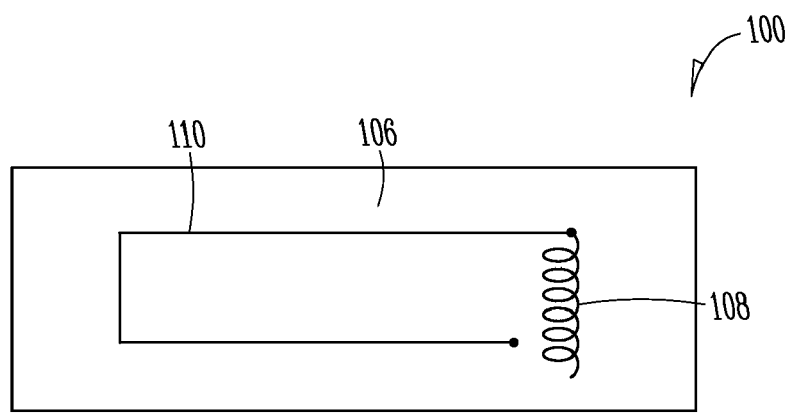
FIG. 1B illustrates a top view of an implantable medical device having radio-frequency telemetry capabilities, according to one embodiment.

FIG. 1B illustrates a top view of an implantable medical device 100 having radio-frequency telemetry capabilities, according to one embodiment. The device includes an antenna 106 having a helical portion 108 and a whip portion 110 to enhance a radiation pattern of the antenna. As shown, the whip portion of the antenna can be curved, linear, or be composed of multiple linear or curved segments, according to various embodiments.

According to various embodiments, the antenna may have many different orientations within the device. For example, the helical portion can have an axis normal to, parallel to, or on a variety of angles to the adjacent surface of the device housing. In addition, the whip portion can be normal to, parallel to, or on a variety of angles to the device housing. Also, the helical portion may be on either end of the whip portion, or anywhere along the whip portion, according to various embodiments. The placement of the whip and helical portions can be positioned to adjust the radiation direction or pattern of the resulting antenna. In addition, the position of the helical portion with respect to the whip portion can change the impedance of the antenna (a conjugate match provides optimal power coupling) and also effects the radiation efficiency of the antenna.

FIG. 2 illustrates an implantable medical device having a dielectric compartment, according to one embodiment. The device 200 includes a housing 202 for containing electronic circuitry. The device also includes a header 204 adjacent a housing surface and a dielectric compartment 212 adjacent a housing surface and adjacent the header 204. An antenna 206 is connected to the electronic circuitry, the antenna having a helical portion 208 embedded in the header and a whip portion 210 embedded in the dielectric compartment. According to various embodiments, the antenna and circuitry are adapted to facilitate far-field transmission and reception of modulated radio-frequency energy at a specified carrier frequency.

According to various embodiments, the compartment 212 includes a first dielectric material and the header 204 includes a second dielectric material. The first and second dielectric material may be the same or a different material. According to various embodiments, the first dielectric material can include a sleeve of alumina, a sleeve of a ceramic, or a high-dielectric constant liquid in a sleeve surrounding the antenna. The dielectric materials need not be high-dielectric constant materials, according to various embodiments. In various embodiments, the dielectric material may include an overmold dielectric material, medical adhesive backfill dielectric material, or circuit board dielectric material. When discussing dielectric material, the dielectric constant "k" is used to describe the relative permittivity of the material. For the purposes of this disclosure, a material with a dielectric constant above 4.0 (the dielectric constant of silicon dioxide) is considered a high dielectric constant material.

Leads 220 protrude from lead bores 222 in the device header, according to various embodiments. In one embodiment, the helical portion of the antenna is positioned within the header opposite the lead bores 222, to take advantage of dead space within the header and to decrease the impact of changes in lead configuration.

The antenna can be made of formed, rolled, stamped or cast metal or conductive composite material and may be a wire, band/ribbon, or hollow structure.

The antenna housing or compartment can be formed, molded, machined or cast plastic or composite material. The antenna and its housing can be mounted internally or externally in either an implantable device or an external communication device, such as the device of FIG. 5, below. The antenna structure can be end-fed in the header or at the base, or any other penetration through the device housing. The antenna can be fed at its end, along its length, and can contain an open or shunt stub termination to the housing or other ground connection. The return path can be capacitive or conductive, and the antenna may include features to enhance capacitive coupling. The antenna can be fed by a waveguiding structure and this feed may include high-voltage isolation.

Figure 3:
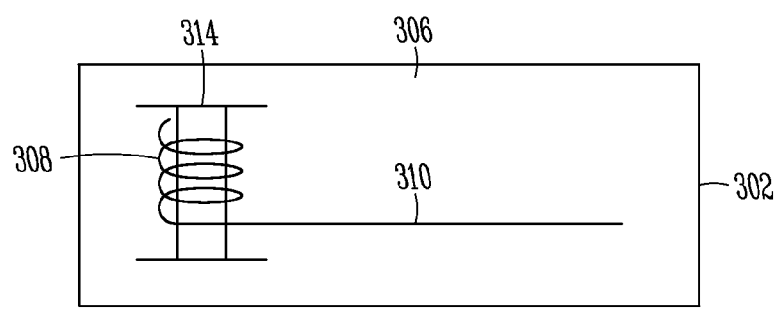
FIG. 3 illustrates a radio frequency antenna having a helical portion wound on a bobbin, according to one embodiment.

FIG. 3 illustrates a radio frequency antenna. The depicted antenna 306 is shown within a connector assembly 302, and has a whip portion 310 and a helical portion 308, according to one embodiment. The connector assembly 302 may include a device header in various embodiments. The helical portion 308 of the antenna includes a metal wire wound around a bobbin 314. According to various embodiments, the bobbin 314 has a dielectric core. The dielectric core of the bobbin 314 can include alumina, a ceramic or a high-dielectric constant liquid, according to various embodiments. The bobbin dielectric materials need not be high-dielectric constant materials, according to various embodiments. In various embodiments, the bobbin dielectric material may include an overmold dielectric material, medical adhesive backfill dielectric material, or circuit board dielectric material.

System for Enabling Radio-Frequency Telemetry in IMD

Figure 4:
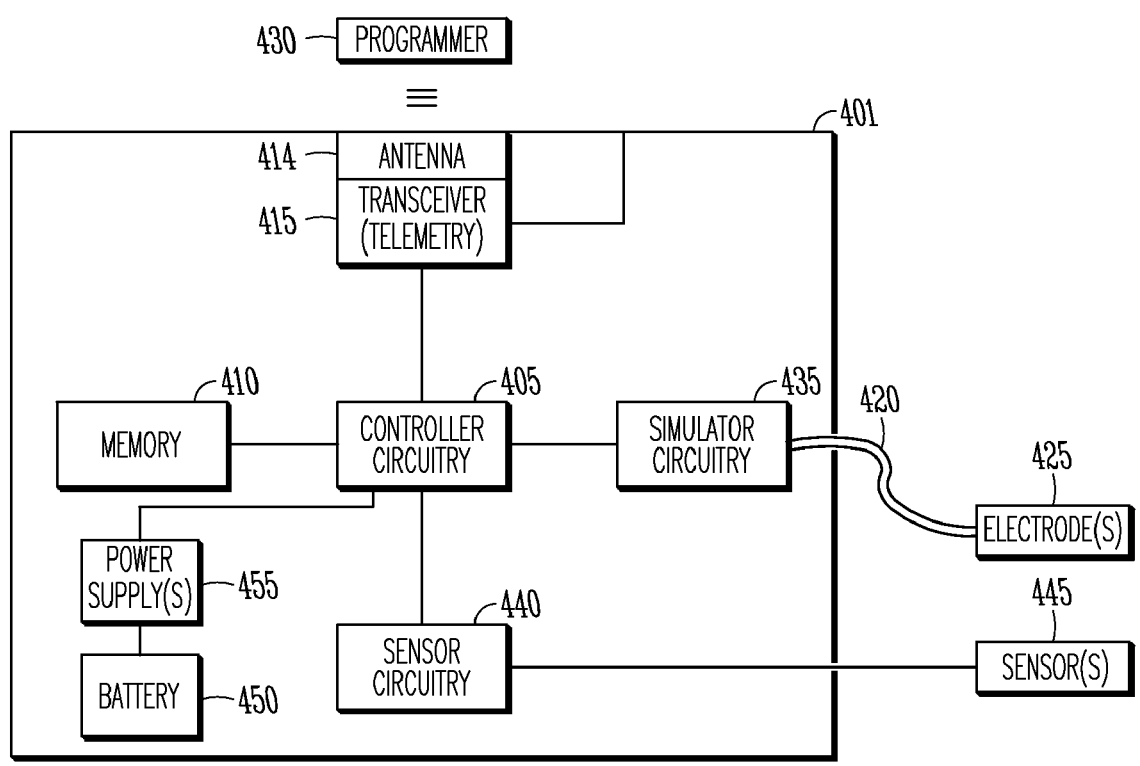
FIG. 4 illustrates a block diagram of a system with an IMD having radio-frequency telemetry capabilities, according to one embodiment.

FIG. 4 illustrates a block diagram of a system with an IMD having radio-frequency telemetry capabilities, according to one embodiment. The system includes an IMD 401, an electrical lead 420 coupled to the IMD 401, and at least one electrode 425. The IMD includes a controller circuit 405, a memory circuit 410, an antenna 414, a telemetry circuit 415, and a stimulation circuit 435. The telemetry circuit 415 can be electrically connected to a conductive portion of the housing 102. At least one battery 450 connects to one or more power supplies 455 to provide electrical power to the device. The depicted power supply 455 is connected to the controller circuit 405. The controller circuit 405 is operable on instructions stored in the memory circuit to deliver stimulation therapy. Therapy is delivered by the stimulation circuit 435 through the lead 420 and the electrode(s) 425 to stimulate the myocardia or a neural target. Other stimulation targets and other types of therapy, such as drug delivery, are within the scope of this disclosure. The telemetry circuit 415 and antenna 414 (such as the antenna depicted in FIG. 1A) allow communication with an external communication, monitoring or control device, such as programmer 430. Other examples of external devices include a bedside monitor or hand-held programming or monitoring device. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 senses one or more physiological parameters and delivers stimulation therapy. The illustrated system also includes sensor circuitry 440 that is coupled to at least one sensor 445. The controller circuit 405 processes sensor data from the sensor circuitry and delivers a therapy responsive to the sensor data.

Figure 5:
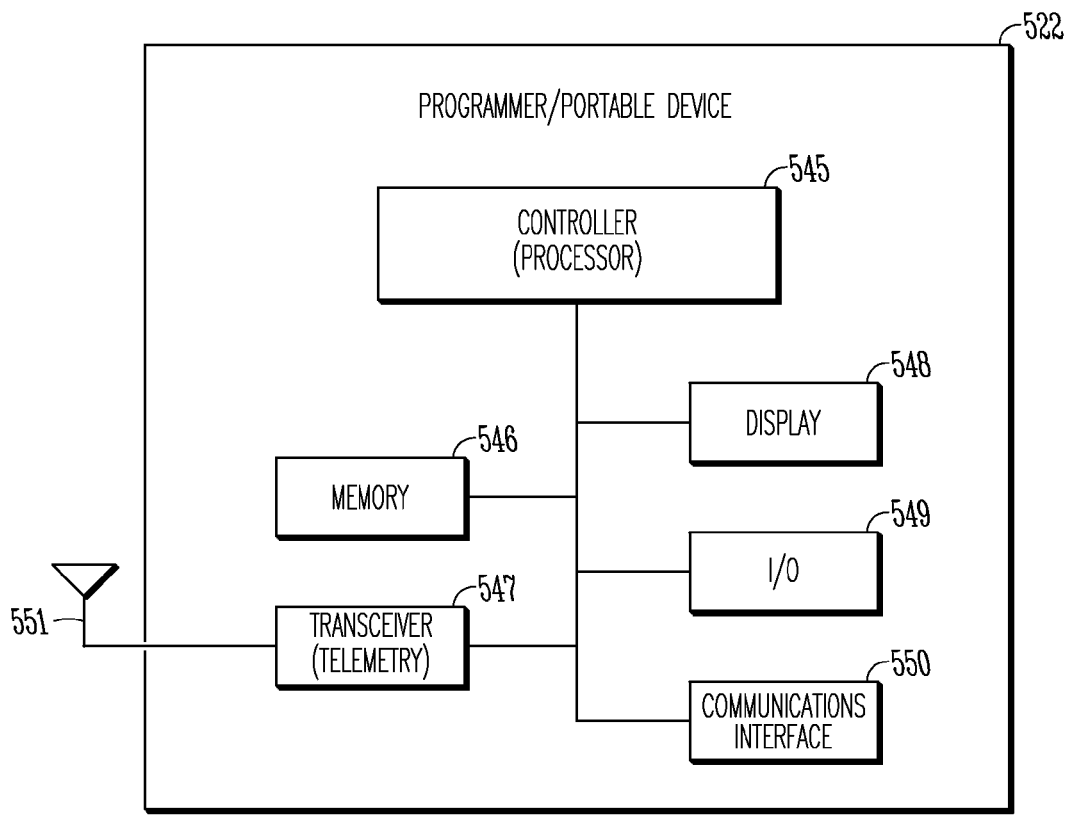
FIG. 5 illustrates a block diagram of an external communication, monitoring or control device such as illustrated in the system of FIG. 4 or other external device to communicate with the IMD(s), according to one embodiment.

FIG. 5 illustrates a block diagram of an external communication, monitoring or control device such as illustrated in the system of FIG. 4 or other external device to communicate with the IMD(s), according to one embodiment. Examples of external communication, monitoring or control devices include programmers, bedside monitors, hand-held programming or monitoring devices, and Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry are connected to an antenna 551 to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Method for Enabling Radio-Frequency Telemetry in IMD

Figure 6:
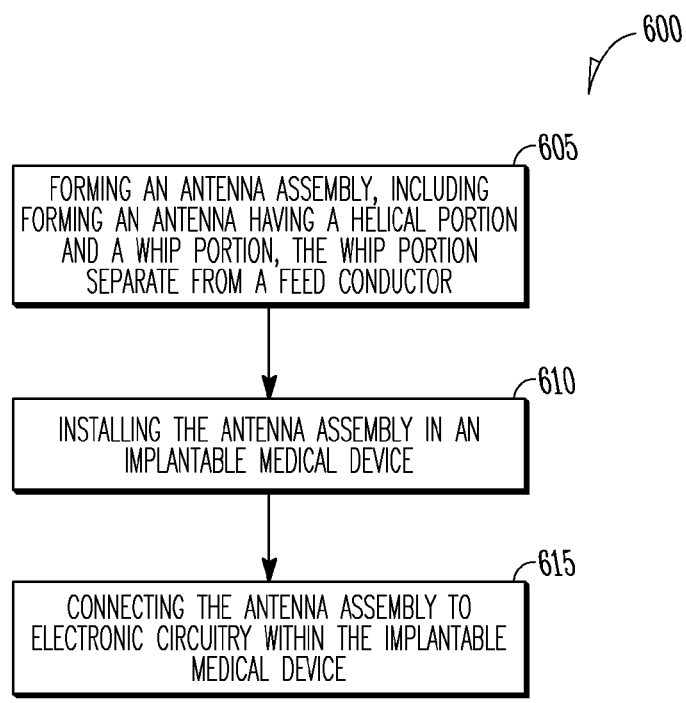
FIG. 6 illustrates a flow diagram of a method for making an IMD having radio-frequency telemetry capabilities, according to one embodiment.

FIG. 6 illustrates a flow diagram of a method for making an IMD having radio-frequency telemetry capabilities, according to one embodiment. According to various embodiments, the method 600 includes forming an antenna assembly, including forming an antenna having a helical portion and a whip portion, the whip portion separate from a feed conductor, at 605. The method embodiment also includes installing the antenna assembly in an implantable medical device, at 610. The method embodiment further includes connecting the antenna assembly to electronic circuitry within the implantable medical device, at 615.

According to one embodiment, forming the antenna assembly includes surrounding the antenna with a dielectric material. According to another embodiment, the antenna is surrounded with a dielectric material after installing the antenna assembly in the IMD. Surrounding the antenna with a dielectric material may include overmolding the antenna, backfilling with a medical adhesive, or use of other types of dielectric materials such as circuit board material, human tissue, and/or high-dielectric constant materials. Installing the antenna assembly in an implantable medical device includes placing the helical portion of the antenna in a device header, according to various embodiments. According to various embodiments, the antenna and circuitry are adapted to facilitate far-field transmission and reception of modulated radio-frequency energy at a specified carrier frequency.

According to various embodiments, the antenna can be formed using stamped metal, rolled metal, formed metal or cast metal. The antenna can also be formed using conductive composite material, according to an embodiment. In one embodiment, the helical portion of the antenna includes a metal wire wound around a bobbin. Forming the antenna includes surrounding the antenna with dielectric-embedded passive (non-driven) elements adapted to change shape of a transmit and receive spatial pattern, according to an embodiment. These passive elements are also referred to as directors, and may be metallic in various embodiments. The passive elements are adapted to tune the antenna for more efficient transmission and receipt of energy over a specified range of frequencies. The dielectric materials used to surround the antenna need not be high-dielectric constant materials, according to various embodiments. In various embodiments, the dielectric material may include an overmold dielectric material, medical adhesive backfill dielectric material, or circuit board dielectric material.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device, comprising:
a telemetry circuit;
an implantable housing configured to contain at least a portion of the telemetry circuit;
an antenna electrically connected to the telemetry circuit, the antenna including a helical portion and a non-helical portion, the antenna configured to wirelessly transfer information electromagnetically using a helical portion that is physically and electrically shorter than a quarter of a wavelength of an electromagnetic wave propagating through a tissue medium having a relative dielectric constant greater than a free space relative dielectric constant;
wherein the axis is a longitudinal axis of the helical portion; and
wherein the helical portion provides an off-axis radiation component.

2. The implantable device of claim 1, wherein the helical portion is physically and electrically shorter than a quarter of a wavelength of an electromagnetic wave propagating through a tissue medium having a relative dielectric constant greater than a free space relative dielectric constant.

3. The implantable device of claim 2, wherein the tissue medium includes muscle tissue.

4. The implantable device of claim 1, comprising a header mechanically attached to the housing, wherein the header includes a first dielectric material.

5. The implantable device of claim 4, wherein the antenna is contained within the header.

6. The implantable device of claim 4, wherein the header includes a second dielectric material configured to surround at least a portion of the antenna.

7. The implantable device of claim 6, wherein the second dielectric material includes a ceramic sleeve having a greater relative dielectric constant than the first material.

8. The implantable device of claim 6, wherein the second dielectric material includes a medical adhesive.

9. The implantable device of claim 1, wherein the specified operating frequency range includes a frequency range between 300 MHz and 1 GHz.

10. The implantable device of claim 1, wherein the housing includes a conductive portion electrically connected to the telemetry circuit.

11. The implantable device of claim 10, wherein the antenna includes a shunt stub to electrically connect the antenna to the housing at a specified location along the length of the antenna, the shunt stub configured to adjust an input impedance of the antenna.

12. The implantable device of claim 11, wherein an adjusted input impedance of the antenna including the shunt stub enhances return loss as compared to an input impedance of the antenna lacking the shunt stub.

13. The implantable device of claim 1, wherein the specified range of frequencies is determined at least in part by a physical arrangement of:
(1) the helical portion of the antenna with respect to at least one of the non-helical portion of the antenna or the housing; or
(2) the non-helical portion of the antenna with respect to at least one of the helical portion of the antenna or the housing.

* * * * *